United States Patent [19]

Holte

[11] 4,325,385
[45] Apr. 20, 1982

[54] PATIENT MONITORING EQUIPMENT

[75] Inventor: Bo Holte, Klampenborg, Denmark

[73] Assignee: Simonsen & Weel's EFTF. A/S, Albertslund, Denmark

[21] Appl. No.: 188,909

[22] Filed: Sep. 19, 1980

[51] Int. Cl.³ .............................................. A61B 5/04
[52] U.S. Cl. ................................................ 128/712
[58] Field of Search ............... 128/630, 668, 670, 671, 128/672, 687, 688, 695, 696, 698, 699, 700, 702, 703, 704, 705, 706, 707, 709, 710, 712

[56] References Cited

U.S. PATENT DOCUMENTS

| | | | |
|---|---|---|---|
| 3,762,398 | 10/1973 | Schefke et al. ...................... | 128/2 R |
| 3,857,383 | 12/1974 | Sommerfeld et al. .............. | 128/630 |
| 3,865,101 | 2/1975 | Saper et al. ......................... | 128/696 |
| 4,006,737 | 2/1977 | Cherry ................................. | 128/702 |
| 4,051,522 | 9/1977 | Healy et al. .......................... | 358/86 |
| 4,096,856 | 6/1978 | Smith et al. ..................... | 128/419 D |

OTHER PUBLICATIONS

"The Lancet", Oct. 13, 1962, p. 759.

Primary Examiner—William E. Kamm
Attorney, Agent, or Firm—John T. Synnestvedt; Kenneth P. Synnestvedt

[57] ABSTRACT

Patient monitoring equipment is disclosed comprising a base unit incorporating an oscilloscope and having connection means for a patient derived ECG signal source, and a plurality of monitoring modules each having means for connection with another signal source representative of other physiological parameters, the modules being adapted to be assembled with the base unit in vertically stacked relation.

18 Claims, 7 Drawing Figures

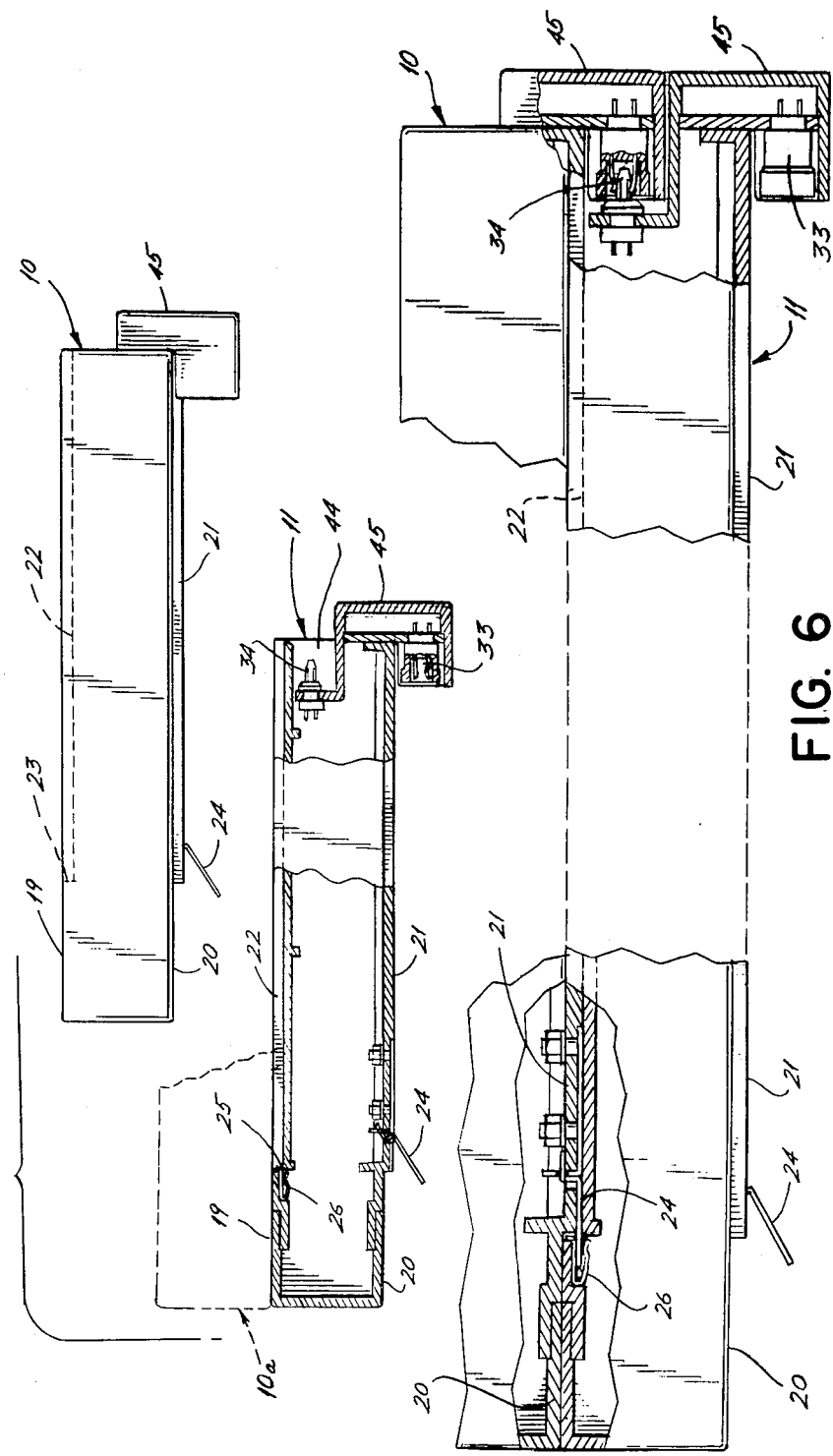

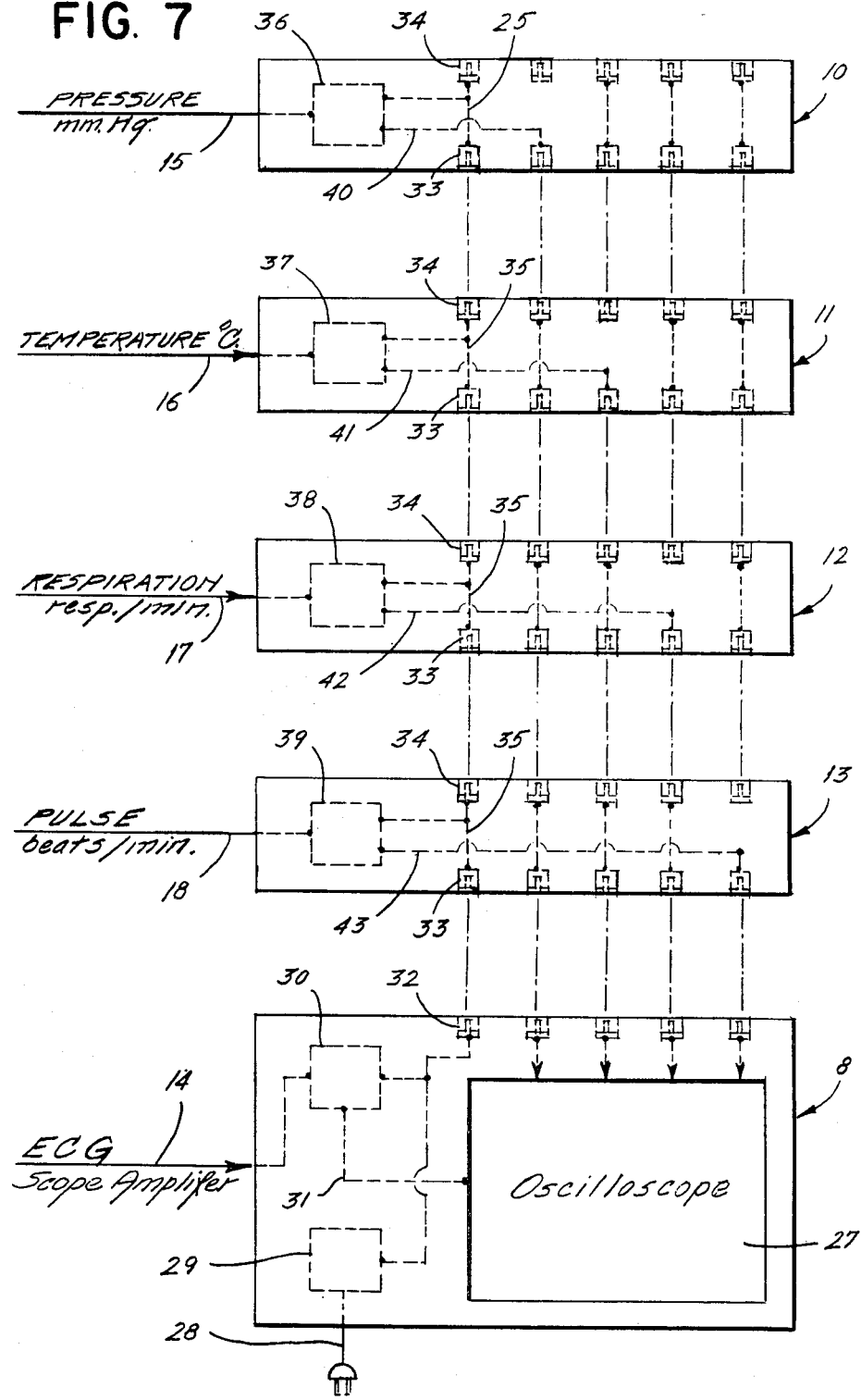

PATIENT MONITORING EQUIPMENT

BACKGROUND AND STATEMENT OF INVENTION

This invention relates to patient monitoring equipment, particularly such monitoring equipment as used in hospitals, especially in intensive care facilities of hospitals.

Many forms of monitoring equipment are known and available, including systems in which provision is made in a console type of installation for the display and monitoring of a plurality of physiological parameters, usually including at least the patient's ECG, blood pressure, temperature and respiration. It has been quite common with equipment of this type to embody a multiplicity of monitoring facilities in a single console type apparatus adapted to be placed in a position adjacent the patient's bed, for instance in an intensive care unit.

It has also been known to incorporate the monitoring facilities for a plurality of patient parameters in a plurality of monitors adapted to be associated with each other. For instance, equipment of this kind has been known in which one unit or module incorporated an oscilloscope, and in which individual modules for the individual parameters were provided, for instance modules for developing signals to be fed to the unit incorporating the oscilloscope, such signals derived from the individual modules being representative of the ECG, blood pressure, temperature, and respiration parameters of the patient.

In most known forms of modular equipment of the kind just mentioned, the module or unit containing the oscilloscope is arranged within a cabinet or case structure having open space laterally at one side of the unit containing the oscilloscope, into which the separate modules for the ECG, blood pressure and other parameters may be inserted.

Although various of these prior art systems are effective in providing the desired monitoring of the several parameters, the prior arrangements are subject to certain disadvantages from a number of standpoints, including achieving maximum efficiency, economy, space utilization and convenient accessability of controls which are desirably provided for the equipment for monitoring the several parameters.

With the foregoing in mind the present invention provides a system having a base unit incorporating an oscilloscope and a multiplicity of modules any or all of which are optionally and alternatively useable with the base unit. According to the present invention the base unit not only incorporates the oscilloscope to be used for visual display of various parameters, but the base unit also incorporates the ECG circuitry and means for connection with a patient derived ECG signal source to be visually displayed. Appropriate power supply connection is, of course, also provided for the base unit.

By incorporating not only the oscilloscope but also the ECG circuitry in the base unit, provision is made for employment of the base unit only in situations requiring only the ECG signal monitoring, which is the parameter most commonly requiring monitoring. Thus, with the ECG monitoring capability incorporated in the base unit containing the oscilloscope, provision is made for monitoring the most commonly required parameter by employment of only a single unit and this is desirable both from the standpoint of equipment costs, and also from the standpoint of space occupied by the equipment, such space ordinarily being a high premium consideration, especially in intensive care units.

In accordance with the invention provision is also made for a plurality of modules or additional units which are adapted to be separably associated with the base unit in a stacked relationship, i.e., with the several modules positioned in superimposed relation to the base unit, rather than in side-by-side relation to the base unit, as in various prior art arrangements. In this way additional modules having means of connection with signal sources representative of other patient parameters may be associated with the base unit without requiring additional space laterally of the base unit, and this is an important consideration, particularly in certain areas such as intensive care units where the plan shape and size of the equipment is an important consideration.

According to the present invention provision is also made for alternative association of any one of several different modules adapted to handle different physiological parameters of the patient, with the base unit; and the invention provides for the stacking of a plurality of modules upon the base unit in any desired sequence, so that if initial monitoring is established with the base unit and any one of several different modules, any one of the other modules may be stacked upon the assembly when it is desired to extend the monitoring to a parameter not previously being monitored. With the equipment provided by the invention, this may be accomplished without removal or disconnection of any of the units already in use.

The foregoing facility for adding modules according to the parameters requiring monitoring provides virtually complete flexibility with respect to the parameters selected for monitoring and thus simplifies and facilitates use of the equipment by the hospital personnel.

The arrangement of the invention is also characterized by a number of additional desirable features including the fact that the physical and electrical connections between the modules and between the modules and the base unit are effected simultaneously by means of a common snap-on motion, which is of great advantage in the use of the equipment.

The interconnection of the modules and base unit also requires the use of no tools; and in addition, no loose connection wires or "pigtails" are employed for interconnections, which is also highly desirable from the standpoint of convenient use of the equipment in congested areas and under circumstances where rapid action may be of importance.

It will be observed that the flexibility of the equipment, including the flexibility of use of various of the modules with the base unit provides a system of connection which is of great importance to the user of the equipment, not merely to the manufacturer of the equipment, as in various prior art systems.

In addition to all of the foregoing, the arrangement of base unit of the present invention as referred to above is highly important from the standpoint of equipment investment required in a given hospital facility in order to provide the needed parameter monitoring for a group of patients. For instance, in use of the equipment of the present invention, a hospital may acquire a group of base units, each of which incorporates facility for ECG monitoring, for use with a group of patients, for instance in an intensive care unit; and a smaller number of the individual modules for the parameters other than the ECG monitoring may be acquired and kept "in stock" for use with individual patients where other parameters require monitoring.

Since all of the parameters other than ECG are used less frequently than the ECG monitoring substantial capital investment may be avoided which would otherwise be required in those monitoring systems of the prior art in which all of the parameters are incorporated in a single unit, regardless of whether or not several of those parameters are needed for a given patient.

BRIEF DESCRIPTION OF DRAWINGS

How the foregoing objectives and advantages are obtained will appear more fully from the accompanying drawings which illustrate a preferred embodiment of the invention. In the drawings:

FIG. 5 is a view illustrating two modules to be interconnected, with the upper module in position with respect to the lower module approaching the position in which interconnection is effected, certain portions of the lower of the two modules here being shown in section, but without illustration of interior electronic components;

FIG. 6 is a view illustrating certain structural arrangements provided for both the physical as well as the electrical interconnection of two superimposed modules, portions being shown in section in order to illustrate the manner in which the interconnections between the modules is effected; and FIG. 7 is a block diagram of a base unit and four modules arranged for assembly in stacked relation.

DETAILED DESCRIPTION

Figure 1:
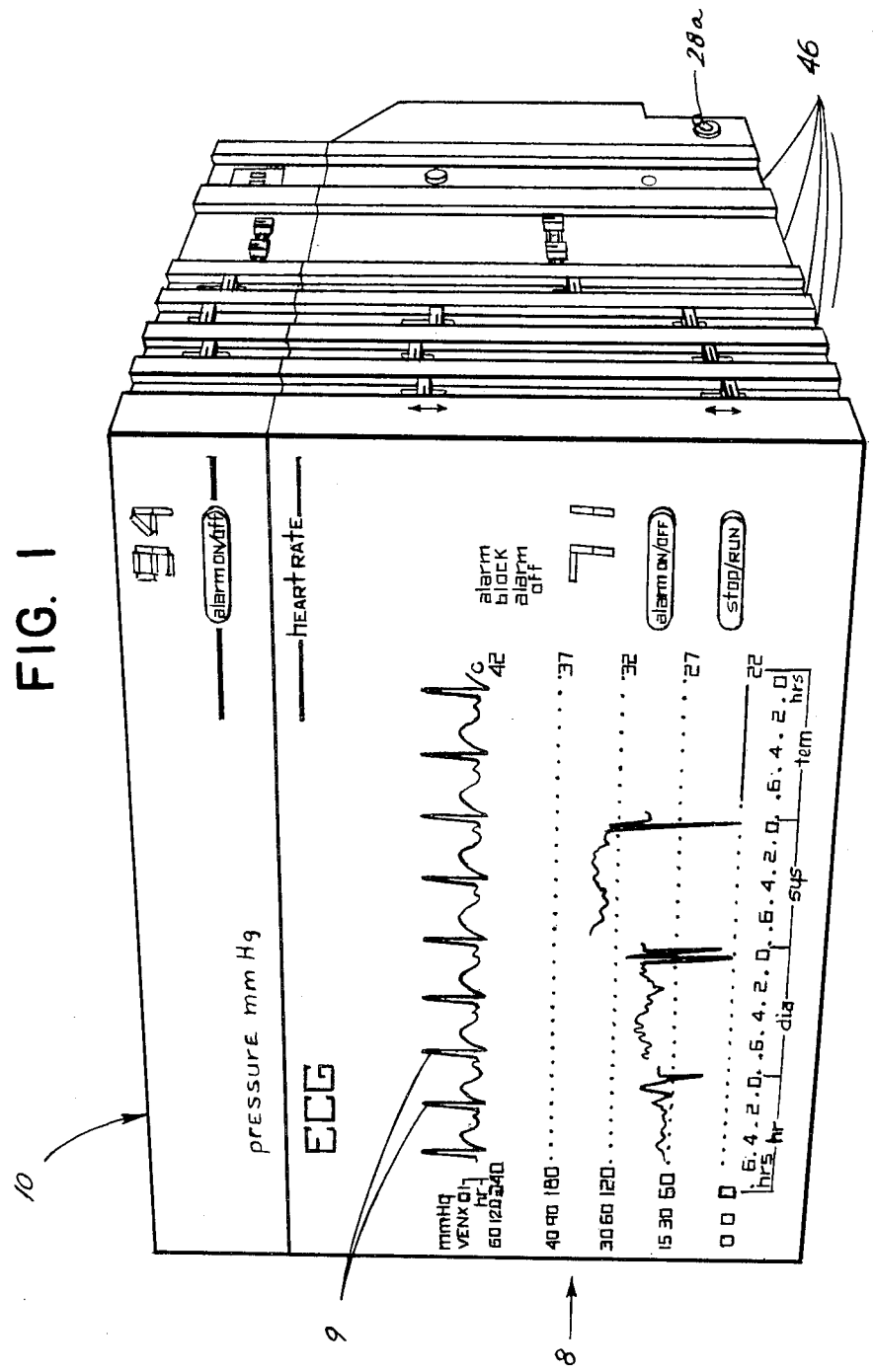
FIG. 1 is a perspective view of a base unit with one module stacked thereon, this view showing the front of the assembly and indicating typical displays appearing on the oscilloscope, the view further showing the right-hand side of the assembly, with controls arranged at that side.

Referring first to FIG. 1, it will be seen that the base unit which is indicated generally at 8, is of generally rectangular shape and encloses monitoring equipment including an oscilloscope arranged for visual observation from the front in order to display various wave forms such as the ECG display indicated at 9. According to the invention, the base unit not only incorporates the oscilloscope but also has connection means for input of a patient derived ECG signal.

Superimposed on the base unit is a module generally indicated at 10, this module being stacked on the base unit with edges of the module generally overlying edges of the base unit. This module, as is indicated by the designation "pressure mmHg" being adapted to provide for monitoring of the patient's blood pressure.

At the righthand side face of both the base unit 8 and the module 10 as shown in FIG. 1, various control devices are provided, some of these being described more fully hereinafter with particular reference to FIG. 2.

Figure 2:
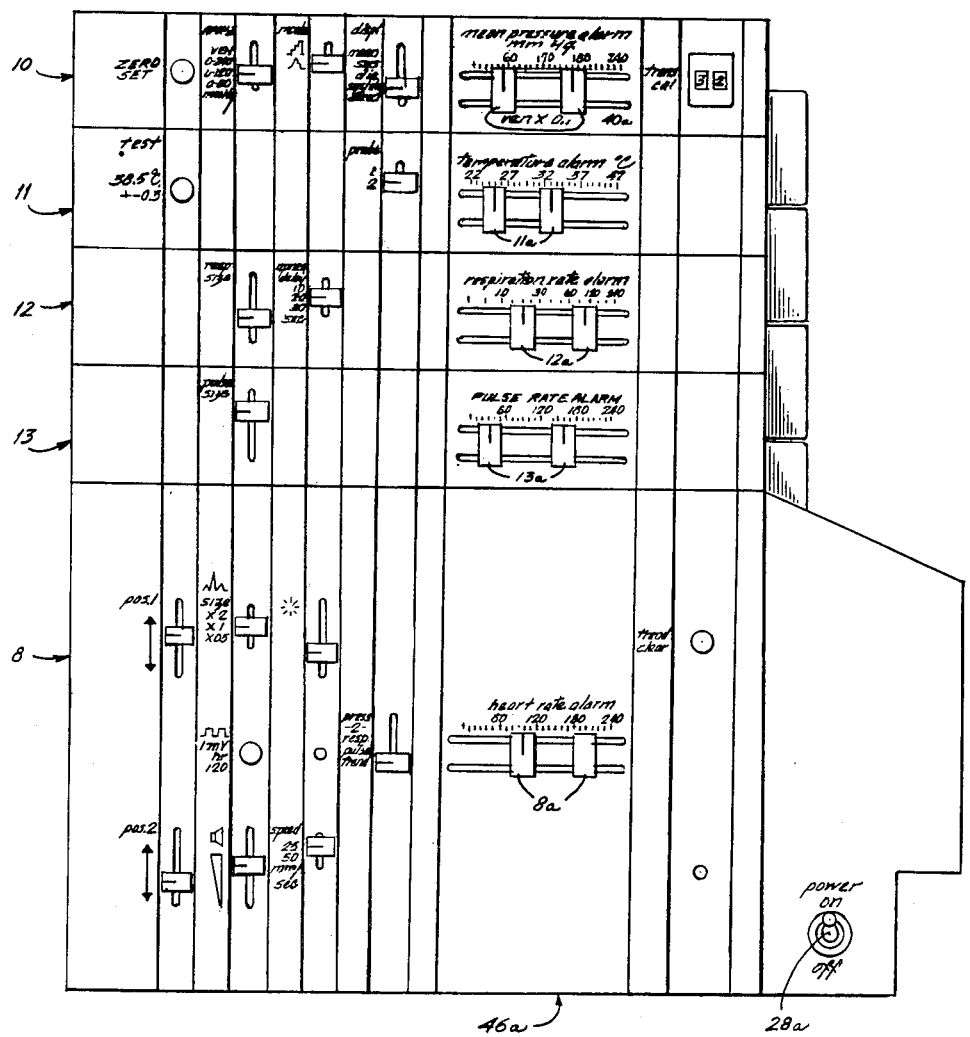
FIG. 2 is an outline elevation view of the righthand side of an assembly of a base unit with four different modules stacked thereon, the righthand side being the side on which many of the controls are arranged.
Figure 3:
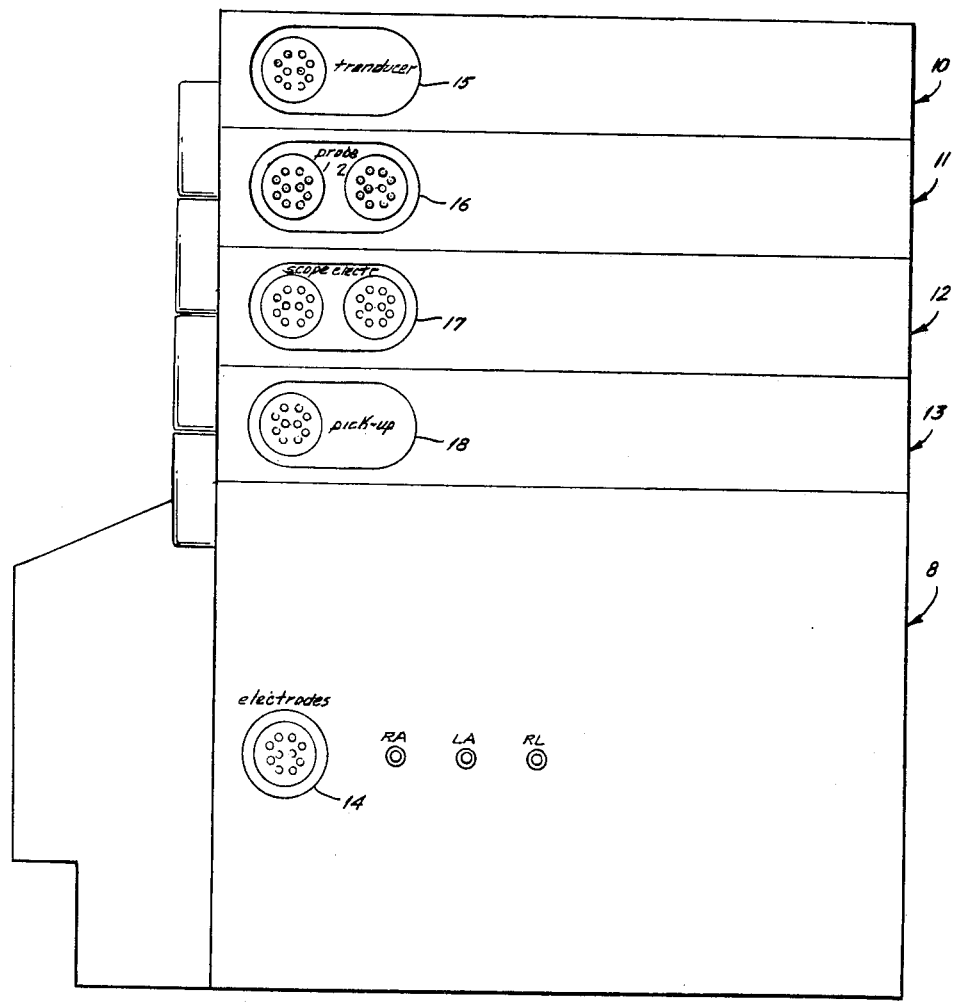
FIG. 3 is a lefthand side view of the assembly shown in FIG. 2 and showing the signal input connectors.
Figure 4:
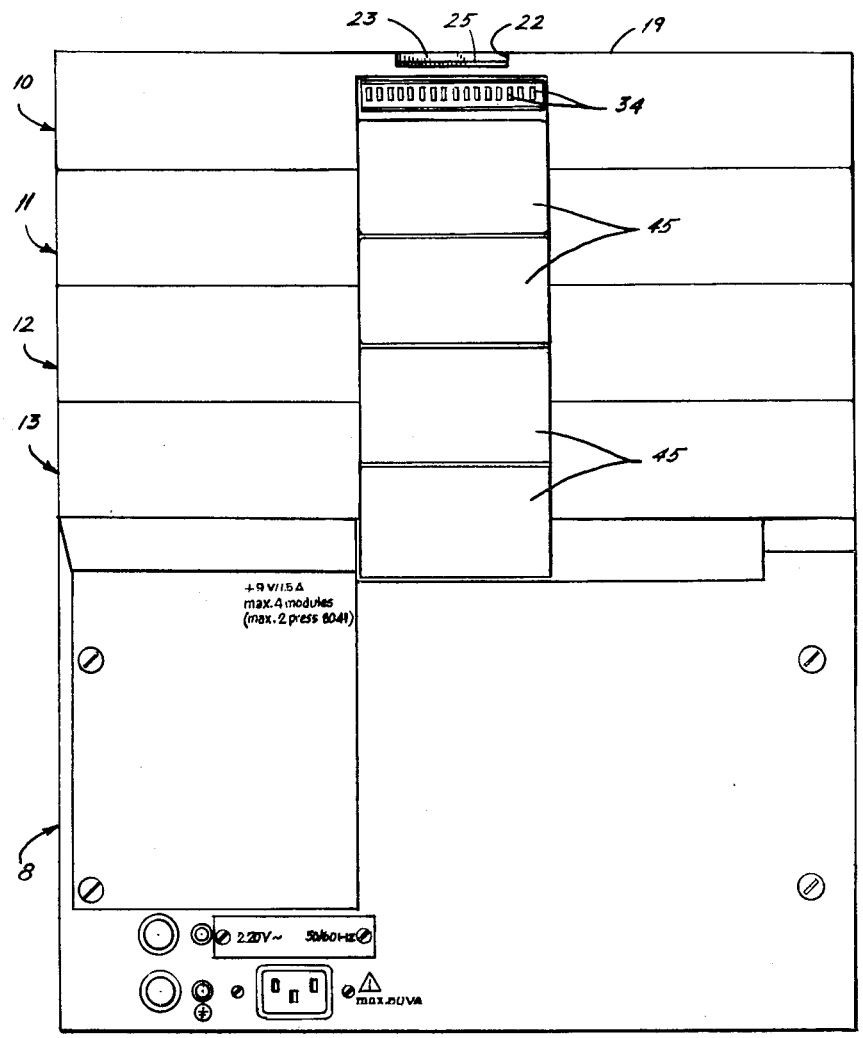
FIG. 4 is a rear elevational view of the assembly shown in FIGS. 2 and 3.

FIGS. 2, 3 and 4 all illustrate an assembly of four different modules with a single base unit, the modules here shown being indicated in these figures by the Reference Nos. 10, 11, 12 and 13, and the base unit by the No. 8.

Similar markings appear on the block diagram of FIG. 7, from which it will be seen that the base unit 8 incorporates means for connection of a patient derived ECG signal source to be visually displayed, this connection also appearing in FIG. 3 at 14. In FIG. 7 each of the modules is adapted for connection with some other signal source representative of another physiological parameter of the patient, i.e., "pressure" for module 10, "temperature" for module 11, "respiration" for module 12 and "pulse" for module 13. The means of connection of the modules with the signal sources is also indicated respectively in FIG. 3 at 15, 16, 17 and 18. It will be noted that in FIG. 1 the "pressure" module 10 is mounted directly upon the base unit 8; whereas in FIGS. 2, 3, 4 and 7, the "pressure" module 10 is stacked upon other modules intervening between the module 10 and the base unit 8. Actually any one of the modules may be mounted directly upon the base unit or upon any other intervening module, with complete freedom of interchangeability, as is explained more fully hereinafter with reference to certain of the other features of the block diagram of FIG. 7.

Certain features of construction of the modules and of the base unit are described herebelow with particular reference to FIGS. 4, 5 and 6, which illustrates mechanical parts by means of which the physical and electrical interconnection of the modules and base unit may be effected.

FIGS. 5 and 6 specifically illustrate the structural parts for effecting the interconnections of two modules, one being superimposed upon the other. Although this description and the illustration in FIGS. 5 and 6 explans these parts with respect to the two modules shown, it is to be understood that certain of those parts are also employed at the top surface of the base unit in order to cooperate with the first module stacked upon the base unit.

Each module comprises upper and lower wall structures 19 and 20, extended throughout the upper and lower surfaces of the module. The lower and upper wall structures of each module are provided with portions formed as tongue and groove elements 21 and 22. When these tongue and groove elements are brought together by superimposing one module upon another, the tongue element at the lower side of the upper module will fit into or engage the groove at the upper side of the lower module. Thus, as seen in the view of FIG. 5, when the upper module (here indicated as module 10) is positioned above and displaced somewhat rearwardly of the lower module (here indicated as module 11), and then is moved downwardly toward the lower module, the tongue 21 on the module 10 will engage in the groove 22 of module 11. The assembly motion of the modules is then continued by shifting the module 10 forwardly, i.e., to the left as viewed in FIG. 5, to the position indicated by dash lines marked 10a in FIG. 5. This assembly motion may readily be accomplished by the hands of the attendant which grasp the upper module 10 at opposite lateral sides thereof, whereupon the module is lowered into position on the subjacent module 11. Since the modules are of the same width, the attendant's fingers conveniently come into contact with the lower module, and this will serve to readily guide the upper module into the proper position with its side edges overlying the side edges of the subjacent module and with the tongue 21 engaging the groove 22.

The assembled relation of the pair of modules described above with relation to FIG. 5 is illustrated in FIG. 6; and from comparison of FIGS. 5 and 6 and the following description, the mechanical and electrical interconnection of these modules may readily be understood. First note that the groove 22 extends forwardly from the rear edge of the module to the abutment indicated at 23, which in effect stops or limits the forward motion of the upper module with respect to the lower module. A latch element 24 is provided on the lower side of the tongue 21 on each module, this latch element being arranged for downward swinging or pivoting under the action of gravity to a position such as indicated in FIGS. 5 and 6, i.e., to a position forming an angle less than 90° from the base of the module. At the forward end 23 of the groove 22 of each module a slot 25 is provided (see also FIG. 4), this slot being located adjacent the bottom of the groove 22 and being of width and height accommodating the latch element 24. The projection of the latch element 24 through this slot being clearly shown in FIG. 6.

In FIG. 6 it will further be seen that a cooperating interior latch element 26 is provided in a position to receive the free end of the latch element 24 when the upper module is shifted forwardly to the position shown in FIG. 6. In this position the edges of the modules being assembled are located in superimposed or overlying relation to each other. Preferably the latch elements 24 and 26 are provided with frictionally interengaging portions, for instance having an aperture or recess in the element 24 engageable by the lower part of the element 26, thereby applying some frictional restraint to separation of the upper module from the lower by rearward movement of the upper module. This aids in stabilizing the modules in assembled relation.

The pivotal mounting of the latch element 24 is desirable in order to assure that upon the assembly of the modules the free or leading edge of the element 24 will engage in the groove 22 and will further enter through the slot 25 at the forward end of the groove 22 during assembly. Moreover, the arrangement of the latch for pivotal movement also provides for automatic "collapse" of the latch upwardly against the bottom of the module when the module is not in use and is being stored on a shelf or other storage surface.

It is contemplated that the base unit 6 shall have on its upper surface a groove 22, slot 25 and interior latch element 26 of the kind described above with respect to FIGS. 5 and 6, so that any one of the modules may be superimposed directly upon the base unit.

The structural parts provided for electrical interconnection of the modules and for connection of the modules with the base unit will be described more fully hereinafter following a description of the block diagram of FIG. 7.

The base unit 8 incorporates the oscilloscope and associated circuitry and this is represented in FIG. 7 by the block marked with the reference numeral 27. The base unit further is provided with means of connection with a power supply indicated at 28, for instance a conventional 110 or 220 volt supply line with 50/60 Hz. An "on/off" switch 28a (see FIGS. 1 and 2) is provided for the power supply.

Preferably a voltage reducing unit indicated at 29 is provided within the base unit, serving to supply the desired current not only to the oscilloscope equipment in the base unit but also to the various signal components incorporated in the individual modules. The base unit as above noted is provided with means for connection with a patient derived ECG signal source as indicated at 14, this signal being delivered through the amplifier 30, from which the signal is delivered to the oscilloscope, by the connection indicated at 31.

Current is delivered from the unit 29 in the base unit to the amplifier 30 and also through connectors diagramatically indicated in FIG. 7 to each of the modules adapted to be associated with the base unit. For this purpose, the base unit is provided with a connector 32 with which a mating connector such as indicated at 33 on each one of the four modules 10, 11, 12 and 13 may be associated. In addition, each of the modules has a connector 34, being interconnected within that module to its connector 33 as indicated at 35. By virtue of this system the desired supply voltage is delivered into each of the modules regardless of the total number of modules used and also regardless of the sequence in which they are assembled or superimposed upon the base unit.

As already mentioned above each of the modules is provided with means for connection of a separate signal source representative of individual physical parameters of the patient other than the ECG, and these signal sources are delivered to the respective circuits or amplifiers 36, 37, 38 and 39, each one of which, as indicated in FIG. 7, derives a voltage supply from the line 35. Each one of these amplifiers is also provided with mating connectors by which the modules may be connected with the oscilloscope in the base unit, these mating connectors being of the same type as the connectors 33 and 34 described above. With four modules as illustrated in FIGS. 2, 3, 4 and 7, the signal circuits 40, 41, 42 and 43 are respectively associated with separate mating connectors adapted to deliver that signal to the oscilloscope in the base unit, regardless of the sequence of stacking of the modules. This is indicated in the block diagram of FIG. 7 and it is pointed out that on each module, two series of connectors are provided, these series being of opposite or mating types. One of the series of connectors conforms with the female type as indicated at 33, and the other with the male type as indicated at 34.

It is to be noted in the block diagram of FIG. 7 that in each of the modules, the signal line (40, 41, 42 or 43) is connected with only the lower mating connector 33 of one of the pairs, all of the other pairs of lower and upper connectors 33 and 34 being interconnected within the module. Because of this pattern, the desired power and signal connections will be established regardless of the sequence in which the modules are stacked; but in addition, in the event that two identical modules are stacked one upon the other, the lower one of those two is the only one which will transmit the signal to the base unit. This feature is of importance in avoiding confusion which might otherwise result in consequence from inadvertent stacking of duplicate modules for a given parameter.

Attention is now directed to the fact that the series of male connectors 34 for the module 11 are shown in FIGS. 5 and 6 toward the rear edge of that module, these connectors being positioned within a socket or recess 44 in the rear edge of module 11, which is adapted to receive a series of female connectors 33 which are suspended by a bracket 45 at the rear edge of the module in position to enter the socket 44, as plainly indicated in FIGS. 5 and 6.

It will be observed from FIGS. 5 and 6 that the interengagement of the connectors 33 and 34 occurs concurrently with the interengagement of the latch elements 24 and 26, thereby providing for concurrent physical and electrical interconnection is also provided for in the assembly of any one of the modules with the base unit; and the concurrent action is also provided for regardless of the sequence of stacking the modules on the base unit.

The provision of the pivoted latch element 24 which assures engagement with the latch 26 when the modules are assembled is of great importance in preventing upward displacement of the forward edge of a given module with respect to an underlying module. Such inadvertant displacement could readily seriously damage the electrical interconnections which are provided adjacent the rear edges of the modules.

Turning now to the location of controls, it will be seen from FIGS. 1 and 2 that most of the controls are concentrated on the right hand side of the equipment.

From FIG. 1, it will be seen that the righthand side of the assembly of base unit and module there shown is contoured, preferably providing vertically extending grooves such as indicated at 46, which grooves extend not only throughout the side wall of the base unit but also throughout the side wall of the module; and from the somewhat diagrammatic view of FIG. 2, it will be seen that all of the modules are similarly contoured and further that the grooves provide for the same general pattern in all of the modules, thereby providing for extension of those grooves throughout the entire height of the assembly, regardless of the number of modules stacked on the base unit.

Various control devices for the base unit and also for the modules are desirably distributed in the grooves above referred to. Although any of a wide variety of known control systems and circuits may be incorporated in the base unit and in the modules, the invention contemplates a concentration of the manually operable control organs for the control systems on the superimposed edges of the modules and the base unit. The specific nature of the controls and the control circuitry forms no part of the present invention and, therefore, is not specifically described or illustrated herein; but it is here noted that the location of the various control organs in certain contoured areas, such as the grooves of the righthand side wall of the assembly, is of advantage because the hand and fingers of the attendant will readily sense the location of the control organs, even while the attendant's visual attention is directed to the wave forms displayed on the front face of the base unit.

Preferably, the distribution of the control organs in the grooves on the control side of the assembly is arranged so that the control organs for similar or functionally related controls are positioned on the sides of the base unit and module in superimposed relation, desirably within the same groove. For example, as seen in FIG. 2, the base unit and each of the four modules there shown are provided with control organs for adjustably establishing the limits of the parameter being monitored beyond which an alarm or danger signal is triggered. Those control organs as shown in FIG. 2 comprise minimum and maximum adjustment devices 8a, 13a, 12a, 11a and 10a; and as there shown, those adjustment devices for the base unit and for each of the modules are located in the same vertically extended area or groove 46a and from the standpoint of convenience and reliability in effecting control adjustments, this vertically superimposed relationship of the control organs which are functionally related to the corresponding patient's parameters in the same general manner, constitutes a significant improvement in equipment of this type. This is true regardless of the specific form of the monitoring equipment and circuits employed.

From the foregoing description of the drawings, it will be seen that the equipment of the present invention achieves numerous important objectives, not only from the standpoint of convenience and reliability of the manipulation of the modules and their controls, but also from the standpoint of the space occupied, the flexibility of the equipment to monitor only one or any of a group of patient parameters, and the accomplishment of all of these objectives in equipment of modular form requiring a reduced total investment as compared with various prior systems while still providing for the monitoring needs of each patient.

I claim:

1. Patient monitoring equipment comprising a base unit having an oscilloscope for visual display of signals representative of a plurality of physiological parameters, the base unit having means for connection of a patient derived ECG signal source to be visually displayed, module adapted to be separably associated with the base unit and having means for connection with a second signal source represenative of another physiological parameter of the. patient, the module being adapted to be assembled with the base unit in stacked relation and with edges generally overlying edges of the base unit, means for physically interlocking the module and the base unit in assembled relation including interengageable means adapted to interlock upon edgewise sliding movement of the module with respect to the base unit in one direction, and means for electrically interconnecting the module and the base unit to provide for visual display of the physiological parameter received from said second signal source, the means for electrically interconnecting the module and the base unit including mating connectors positioned on the base unit and on the module in positions providing for electrical interconnection by edgewise sliding movement of the module with respect to the base unit in the same direction providing for physical interconnection of the module with the base unit, thereby providing for concurrent electrical and physical interconnection of the module with the base unit.

2. Patient monitoring equipment comprising a base unit having an oscilloscope for visual display of signals representative of a plurality of physiological parameters, the base unit having means for connection of a patient derived ECG signal source to be visually displayed, a plurality of modules adapted to be separably associated with the base unit and respectively having means for connection with other signal sources representative of other physiological parameters of the patient, the modules being adapted to be assembled with the base unit in serially stacked relation with edges of the modules overlying edges of each other and of the base unit, means for physically interlocking the modules and the base unit in assembled relation, including interengageable means on the base unit and on each module adapted to interchangeably interlock alternatively with each other in any superimposed relation of the modules being stacked upon the base unit upon relative edgewise sliding movement of any module with respect to the base unit or with respect to any other module in one direction, and means for electrically interconnecting the modules and the base unit to provide for visual display of the parameters received from said other signal sources, the means for electrically interconnecting the modules and the base unit including mating connectors positioned on the base unit and on the modules in positions providing for electrical interconnection by edgewise sliding movement of a module, alternatively with respect to the base unit or with respect to another module in the same direction providing for physical interconnection of a module with the base unit or alternatively with another module, thereby providing for concurrent electrical and physical interconnection of a module either with the base unit or alternatively with another module.

3. Patient monitoring equipment comprising a base unit having an oscilloscope for visual display of signals representative of a plurality of physiological parameters, the base unit having means for connection of a patient derived ECG signal source to be visually displayed, a module adapted to be separably associated with the base unit and having means for connection with a second signal source representative of another physiological parameter of the patient, the module being adapted to be assembled with the base unit in stacked relation and with edges generally overlying edges of the base unit, means for physically interlocking the module and the base unit in assembled relation including interengageable means adapted to interlock upon edgewise sliding movement of the module with respect to the base unit in one direction, and means adjacent overlying edges of the module and base unit at one side thereof for electrically interconnecting the module and the base unit to provide for visual display of the physiological parameter received from said second signal source, said interengageable means being spaced from the electrical interconnecting means and including a latch mounted on the underside of the module, the base unit having a latch receiving orifice in an upper portion thereof, and the latch and orifice being relatively oriented to provide for engagement of the latch in the orifice upon relative sliding movement of the module and base unit in said one direction.

4. Equipment as defined in claim 3 in which the latch is mounted on the module with freedom for limited downward movement prior to engagement of the latch in the orifice, thereby providing for engagement of the latch in the orifice even with the module spaced above the base unit.

5. Equipment as defined in claim 4 in which the latch is pivotally mounted for downward movement by gravity and further including means limiting downward pivoted movement of the latch to a range less than 90°.

6. Patient monitoring equipment comprising a base unit having an oscilloscope for visual display of signals representative of a plurality of physiological parameters, the base unit having means for connection of a patient derived ECG signal source to be visually displayed, a module adapted to be separably associated with the base unit and having means for connection with a second signal source representative of another physiological parameter of the patient, the module being adapted to be assembled with the base unit in stacked relation with edges generally overlying edges of the base unit, means for physically interlocking the module and the base unit in assembled relation including interengageable means adapted to interlock upon edgewise sliding movement of the module with respect to the base unit in one direction, means adjacent overlying edges of the module and base unit at one side thereof for electrically interconnecting the module and the base unit to provide for visual display of the physiological parameter received from said second signal source, said interengageable means being spaced from the electrical interconnecting means and including latch elements mounted on the base unit and module arranged to provide for engagement of the latch elements upon relative sliding movement of the module and base unit in said one direction, and the base unit and module having interfitting tongue and groove shaped portions extended on axes paralleling said one direction of movement, thereby providing for guided relative movement of the module and base unit during said relative sliding movement.

7. Equipment as defined in claim 6 in which the means for electrically interconnecting the base unit and the module and the latch elements are located toward opposite ends of said tongue and groove shaped portions of the base unit and module.

8. Patient monitoring equipment comprising a base unit having an oscilloscope for visual display of signals representative of a plurality of physiological parameters, the base unit having means for connection of a patient derived ECG signal source to be visually displayed, a plurality of modules adapted to be separably associated with the base unit and respectively having means for connection with other signal sources representative of other physiological parameters of the patient, the modules being adapted to be assembled with the base unit in serially stacked relation and with edges of the modules overlying edges of each other and of the base unit, means for physically interlocking the modules and the base unit in assembled relation, including interengageable means on the base unit and on each module adapted to interchangeably interlock alternatively with each other in any superimposed relation to the modules being stacked upon the base unit, and means for electrically interconnecting the modules and the base unit to provide for visual display of the parameters received from said other signal sources, the means for electrically interconnecting the modules and the base unit including mating connectors positioned on the base unit and on the modules in positions providing for electrical interconnection of an upper module with the base unit through an intervening module.

9. Equipment as defined in claim 8 in which each module has electrical interconnecting means providing for connection of any one of the modules with the base unit through any module stacked in a position intervening between said one module and the base unit.

10. Patient monitoring equipment comprising a base unit having an oscilloscope for visual display of signals representative of a plurality of physiological parameters, the base unit having means for connection of a patient derived ECG signal source to be visually displayed, a plurality of modules adapted to be separably associated with the base unit and respectively having means for connection with other signal sources representative of other physiological parameters of the patient, the modules being adapted to be assembled with the base unit in serially stacked relation with edges of the modules overlying edges of each other and of the base unit, means for physically interlocking the modules and the base unit in assembled relation, including interengageable means on the base unit and on each module adapted to interchangeably interlock alternatively with each other in any superimposed relation of the modules being stacked upon the base unit or with respect to any other module, and means for electrically interconnecting the modules and the base unit to provide for visual display of the parameters received from said other signal sources, the base unit and a plurality of modules each having at least one manually adjustable control positioned at sides thereof adjacent vertically overlying edges, so that said controls are presented in the same general direction laterally of the assembly of base unit and modules.

11. Patient monitoring equipment comprising a base unit having an oscilloscope for visual display of signals representative of a plurality of physiological parameters, the base unit having means for connection of a patient derived ECG signal source to be visually displayed, a plurality of modules adapted to be separably associated with the base unit and respectively having means for connection with other signal sources representative of other physiological parameters of the patient, the modules being adapted to be assembled with the base unit in serially stacked relation with edges of the modules overlying edges of each other and of the base unit, means for physically interlocking the modules and the base unit in assembled relation, including interengageable means on the base unit and on each module adapted to interchangeably interlock alternatively with each other in any superimposed relation of the modules being stacked upon the base unit or with respect to any other module, and means for electrically interconnecting the modules and the base unit to provide for visual display of the parameters received from said other signal sources, the base unit and at least one module each having a plurality of manually adjustable controls positioned at sides thereof in regions of said vertically overlying edges, so that said controls are presented in the same general direction laterally of the assembly of base unit and modules, and the base unit and the module each having a control functionally related to the corresponding patient parameter in the same general manner, and said functionally related controls being positioned on said sides of the base unit and module in superimposed relation, so that accessibility for manual adjustment is provided in superimposed areas of the same side of the assembly of the base unit and module.

12. Equipment as defined in claim 11 in which the oscilloscope of the base unit is presented toward the front side of the assembly and in which the overlying sides of the base unit and module with which the controls are associated are presented toward one of the lateral sides of the assembly adjoining the front side.

13. Equipment as defined in claim 11 in which the overlying sides of the base unit and module with which the controls are associated are provided with vertically grooved portions in vertical alignment with each other thereby facilitating manual engagement of the controls by manually sensing said grooved portions.

14. Equipment as defined in claim 11 in which said functionally related controls comprise controls for adjustably setting alarm limits for parameter ranges.

15. Patient monitoring equipment comprising a base unit having an oscilloscope for visual display of signals representative of a plurality of physiological parameters, a module adapted to be separably associated with the base unit and having means for connection with a signal source representative of a physiological parameter of a patient, the module being adapted to be assembled with the base unit in stacked relation and with edges generally overlying edges of the base unit, means for physically interlocking the module and the base unit in assembled relation including interengageable means adapted to interlock upon edgewise sliding movement of the module and with respect to the base unit in one direction, and means adjacent overlying edges of the module and base unit at one side thereof for electrically interconnecting the module and the base unit to provide for visual display of the physiological parameter received by said module, said interengageable means being spaced from the electrical interconnecting means and including a latch mounted on the underside of the module, the base unit having a latch receiving orifice in an upper portion thereof, and the latch and orifice being relatively oriented to provide for engagement of the latch in the orifice upon relative sliding movement of the module and base unit in said one direction.

16. Patient monitoring equipment comprising a base unit having an oscilloscope for visual display of signals representative of a plurality of physiological parameters, a plurality of modules adapted to be separably associated with each other and each having means for connection with a signal source representative of a physiological parameter of a patient, the modules being adapted to be assembled in superimposed stacked relation and with edges generally overlying each other, means for physically interlocking the modules in assembled relation including interengageable means adapted to interlock upon edgewise sliding movement of an upper module with respect to a lower module in one direction, and means adjacent overlying edges of the modules at one side thereof for electrically interconnecting the modules, said interengageable means being spaced from the electrical interconnecting means and including a latch mounted on the underside of the upper module, the lower module having a latch receiving orifice in an upper portion thereof, and the latch and orifice being relatively oriented to provide for engagement of the latch in the orifice upon relative sliding movement of the upper module with respect to the lower module in said one direction.

17. Patient monitoring equipment comprising a base unit having an oscilloscope for visual display of signals representative of a plurality of physiological parameters, a plurality of modules adapted to be separably associated with the base unit and respectively having means for connection with signal sources representative of various physiological parameters of the patient, the modules being adapted to be assembled with the base unit in serially stacked relation, means for physically interlocking the modules and the base unit in assembled relation, including interengageable means on the base unit and on each module adapted to interchangeably interlock alternatively with each other in any superimposed relation of the modules being stacked upon the base unit, and means for electrically interconnecting the modules and the base unit to provide for visual display of the parameters received from said signal sources, the means for electrically interconnecting the modules and the base unit including mating connectors positioned on the base unit and on the modules in positions providing for electrical interconnection of an upper module with the base unit through an intervening module, the mating connectors of each module being arranged in upper and lower series adapted to cooperate respectively with the lower and upper series of adjacent modules in the stacked assembly, the connection means for the signal source associated with each module being coupled with only a downwardly presented mating connector, and the other upper and lower mating connectors of that module being interconnected in pairs within the module.

18. Patient monitoring equipment comprising a base unit incorporating a power supply, a plurality of modules adapted to be separably stacked upon the base unit and each having means for connection with a signal source representative of a physiological parameter of a patient, the modules being adapted to be assembled in superimposed stacked relation and with edges generally overlying each other and overlying edges of the base unit, means for physically interlocking the modules in assembled relation including interengageable means adapted to interlock upon edgewise sliding movement in one direction of an upper module with respect to the base unit or to a lower module, and means for electrically interconnecting said power supply with the modules upon relative sliding movement of a module in said one direction.

* * * * *